United States Patent [19]

Vadgama et al.

[11] Patent Number: 5,749,832
[45] Date of Patent: May 12, 1998

[54] MONITORING SYSTEMS

[75] Inventors: Pankaj Madganlal Vadgama, Manchester; Paul William Crump, Brinsworth, both of United Kingdom

[73] Assignee: The Victoria University of Manchester, Manchester, England

[21] Appl. No.: 256,981

[22] PCT Filed: Jan. 28, 1993

[86] PCT No.: PCT/GB93/00163

§ 371 Date: Oct. 6, 1994

§ 102(e) Date: Oct. 6, 1994

[87] PCT Pub. No.: WO93/14693

PCT Pub. Date: Aug. 5, 1993

[30] Foreign Application Priority Data

Feb. 1, 1992 [GB] United Kingdom .................... 9202172
Feb. 28, 1992 [GB] United Kingdom .................... 9204253

[51] Int. Cl.$^6$ ................................................. A61B 5/00
[52] U.S. Cl. ................................... 600/345; 600/372
[58] Field of Search .................................. 128/635, 640, 128/641, 642, 636; 600/345, 346, 347–350, 372

[56] References Cited

U.S. PATENT DOCUMENTS

| | | | |
|---|---|---|---|
| 3,912,614 | 10/1975 | Spracklen et al. | |
| 4,803,991 | 2/1989 | Alena et al. | 128/635 |
| 4,813,424 | 3/1989 | Wilkins | 128/635 |
| 4,834,101 | 5/1989 | Collison et al. | |
| 5,171,689 | 12/1992 | Kawaguri et al. | 128/635 |
| 5,354,448 | 10/1994 | Markle et al. | 128/635 |

FOREIGN PATENT DOCUMENTS

| | | |
|---|---|---|
| 50035 | 4/1982 | European Pat. Off. . |
| 64970 | 11/1982 | European Pat. Off. . |
| 2045940 | 11/1980 | United Kingdom . |

*Primary Examiner*—Robert L. Nasser
*Attorney, Agent, or Firm*—Pillsbury Madison & Sutro LLP

[57] ABSTRACT

Method and electrode assemblies for using or installing an electrode (especially enzyme electrode) in vivo, in which a protecting medium is introduced at the installation site to suppress adverse effects on the electrode's output. The medium is preferably an isotonic solution (e.g. saline) and/or a buffer solution and/or an anti-coagulant, and may be of increased viscosity (e.g. a gel or hydrogel), and may be coated on the electrode assembly. The preferred electrode assembly is a needle within a trocar cannula, preferably with the needle tip set back to form a recess to contain gelled medium which can then be fed with liquid medium. The assembly can be made as a sterilised, sealed pack bearing calibration and/or other data relevant to its use, especially in machine-readable form.

17 Claims, No Drawings

MONITORING SYSTEMS

This invention relates to improvements relating to monitoring systems, and more particularly to improvements relating to systems for monitoring various body parameters, and especially tissue parameters, in vivo by use of electrodes.

BACKGROUND OF THE INVENTION

It is known to use electrodes as part of systems for monitoring a variety of parameters in biological conditions or in biological products or materials, especially as sensors. An especially useful form of electrode for such purposes is in the monitoring of glucose in body fluids, for example in blood or tissue, and to do this either with samples taken from a subject and studied in vitro or by use of the electrode sensor in vivo.

However, though such electrodes work well in vitro there is a major problem in in vivo use which arises from the time required for the stabilisation of the electrode—i.e. the time required for the signals from the electrode, when placed in vivo, to reach a condition in which the signals cease changing even though the environment around the electrode is not changing. This time delay can be as much as several hours, which effectively prevents use under conditions requiring rapid deployment. Also, in the case of electrodes measuring glucose or other components involving an oxidation/reduction process, there can be a considerable depression of the signal response under in vivo conditions, so that there is poor correlation between the signals and measurements of the same amounts or concentrations of analytes under in vivo and in vitro conditions.

It can be seen that such effects are not satisfactory for accurate use in vivo and can restrict severely the usefulness of such electrodes under in vivo conditions despite their otherwise valuable properties when used under in vitro conditions.

There is, therefore, a considerable need for some form of the electrodes or method of use or which can overcome these disadvantages and allow reliable and convenient use in vivo.

The reason for this "read-out" depression of the signal from the electrode is not known, but we believe it arises from some barrier or interference to its activity which is set up when the electrode is put directly into contact with compact biological tissues when it is introduced into a bodily environment.

SUMMARY OF THE INVENTION

We have now found that these disadvantages can be overcome by introducing a liquid medium into the site in vivo at which the electrode is to be used, so that the liquid medium introduced can produce an compatible environment for the electrode. This may be as a prelude to the bodily fluids making contact with the electrode, but may be at any convenient moment before, during or after such contact.

Thus according to our invention we provide a method for using or installing an electrode in place in vivo which comprises the step of providing, at the site of introduction of the said electrode, a protecting medium which, without injuring the biological environment, suppresses the adverse depressive effect on the electrode's output induced by the hostile biological environment when it has not been modified by the protecting medium. This protecting medium may then be modified or replaced by an aqueous surrounding medium which allows the electrode to become exposed to the bodily biochemical changes of the surrounding environment which is to be monitored.

This protecting medium is found helpful by overcoming the fact that tissues themselves can present an environment low in water and high in protein and elastic connective tissue macromolecules (collagen, elastin, glycoproteins) and also surface-active proteins which tend to foul electrode surfaces. All of these distort the normal "aqueous solution" conditions used to calibrate the sensor in vitro. The protecting medium is intended to provide a protecting or less hostile environment in which the electrode can function.

DETAILED DESCRIPTION OF THE INVENTION

It is believed that this protecting medium may act in one or more ways, though they are not fully understood. The protection may be mechanical, chemical or bio-physical, or any combination of one or more of these. In its simplest form, it protects the surface of the electrode so that it makes minimal contact with any medium which produces adverse effects on the electrode's performance before it makes contact with the medium in vivo it is to monitor. The "adverse effects" may be, for example, compression by tissue which may squeeze a necessary aqueous film on the electrode surface (or its membrane), or the developments of an air space around the electrode—for example in blood, bone or cartilage, but especially in subcutaneous tissue which physically prevents contact with the tissue to be monitored. Chemically, it may be the effect of air or oxygen, which may act adversely by its action on the electrode. Thus, for example, air or oxygen (or even nitrogen) may form a layer which physically impedes access of the medium to be monitored, or it may affect the processes by which the electrode operates, or it may even interfere with the medium to be monitored so as to block its access to the electrode, for example by leading to dehydration by evaporation at the membranes.

An additional problem can be that a high concentration of blood components leads to local coagulation and thereby forms a "skin" or barrier of relatively impermeable material which then hinders the access of the materials to be monitored to the electrode surface. This will be made worse if the material (coagulum) is itself then in contact with a surrounding layer of air and then totally or partially dehydrates to form a denser or less permeable barrier.

A preferred method for providing the required environment is to maintain adjacent to the electrode surface a zone containing a protecting medium, which may be one or more of the following:

(a) an isotonic solution, substantially isotonic with the in vivo medium to be monitored (for example having mOsm of 275–295);

(b) a buffer solution, compatible with the in vivo medium to be monitored, to avoid large pH changes which in turn may affect the electrode signal size; and/or (c) an anti-coagulant, which serves to reduce the chances of coagulation over the surface of the electrode or any part of its structure (e.g. over its membrane).

The isotonic solution (a) may be a simple aqueous saline (sodium chloride) solution, or it may contain additives. Such additives may be any conventional pharmaceutically acceptable additives compatible with saline solutions and useful for modifying or improving them, for example to preserve or sterilise them. Simple examples include potassium ion, lactate (as in Hartmann's Solution) and bicarbonate. Further examples include agents to reduce inflammation (e.g.

cortisol), analgesics or other agents to reduce pain (e.g. procainamide), agents which render tissues more permeable to liquids or electrolytes (e.g. hyaluronidase) and so can "open up tight tissues" to provide freer permeability, agents to reduce bacterial growth (e.g. antibiotics), and mixtures or combinations thereof.

Other components which may be used, in solution or suspension, include compounds (for example perfluorocarbons and/or lipids) which dissolve oxygen and so can serve as reservoirs for oxygen to prevent oxygen starvation and/or the oxygen and/or co-factors necessary for the functioning of an oxidase-based enzyme electrode; anti-oxidants, surfactants and many others, provided always that they are pharmaceutically acceptable and do not—by their nature or their concentration—cause any unacceptable, undesirable or adverse effect.

Any "active" components used [i.e. those intended to produce effects, and especially effects other than as components (a), (b) or (c) above] may if desired be in any convenient or conventional form, for example a "slow-release" or other form which can reduce re-absorption by the circulation. An example of such a "slow release" form is that of liposomes enclosing the relevant active ingredient or ingredients.

The buffer solution may contain any pharmaceutically acceptable buffering components but especially may be based on phosphates in known manner (e.g. a mixture of mono-sodium and di-sodium phosphates) and aimed at producing or maintaining a pH of about 7.0 to 7.8.

Preferably, however, an isotonic buffer solution is used.

When an anti-coagulant is used this may be a natural product (for example heparin, hirudine, prostaglandin) or a synthetic product (for example ethylenediamine tetracetic acid—commonly referred to as "EDTA"—or an analogue or derivative thereof; such compounds may be conveniently referred to as carboxylated amine compounds). Mixtures of such materials may be used if desired.

An especially useful class of component is a material which can raise the viscosity of the liquid, either by simply increasing the, viscosity or by forming a gel or hydrogel. These assist in retaining or localising the added protective medium and by increasing the ability to maintain a sufficiently aqueous medium adjacent to the electrode (e.g. by attracting water by osmosis) so as to facilitate its functioning consistently. Higher viscosity leads to a viscous solution which can be held in a stable manner around the electrode; this can assist the liquid medium to remain localised where it is required, i.e. mainly near to the electrode surface, and reduce surface fouling. Indeed, it is useful to use these (especially the hydrogels) to coat the surface of the electrodes (the active electrode surface itself, or any membrane surface around it, enclosing or surrounding it.

It is also advantageous for such gels to be adherent, i.e. able to form an adherent layer on the surface of the electrode or a part of the electrode assembly (e.g. on a surrounding membrane).

Such viscosity-enhancing components may be monomers (e.g. glycerol, mannitol) or soluble macromolecules or polymers, of natural or synthetic nature (e.g. polyvinyl alcohol, poly-HEMA [poly-hydroxyethyl-methacrylate], albumin, dextran, gelatin, hetastarch) or mixtures thereof. Indeed, they may be any materials which can form or constitute non-toxic gels or hydrogels.

One form of the present invention which can be especially useful is a combination of a hydrophilic gel and a supply of liquid medium (e.g. isotonic solution) to the gel layer. This supply of solution may be continuous or discontinuous, as may be found most appropriate for the particular circumstances of use. This assists in maintaining liquid in a layer around the electrode.

Examples of electrodes which may be used include most of the conventional electrodes and electrode systems, for example:

(a) any of the metals (in the form of the element or a compound) used for the study of electrochemically active species (e.g. silver, platinum, or any other base metals which are useful for the study of active species, for example ascorbate, paracetamol, etc.), membrane-covered electrodes using such metals and membranes of such materials as ion-exchange polymers or materials of controlled porosity. These include materials such as the polyether sulphone (PES), polyvinyl chloride (PVC) and commercially available products such as Nafion; these can be used in conjunction with neuro-transmitters (e.g. noradrenalin, dopamine);

(b) oxidase-based enzyme electrodes, in which the oxidisable species may be for example glucose, lactate, etc.);

(c) de-hydrogenase-based enzyme electrodes (For these, the liquid supply to them may be a source of the co-factor (reagent) to facilitate the functioning of the electrode);

(d) oxygen electrodes; these are similar to the enzyme electrodes but can be operated at higher voltages, e.g. approximately +0.6 v against a Ag/AgCl reference electrode.

The medium may be applied in a variety of ways, and one very convenient way is to introduce it into the site in which the electrode is to be used but before the electrode is inserted in place. Such introduction may be by conventional means, such as injection or infusion. This can be achieved using conventional equipment, for example hypodermic needles and the like, especially as these can be used to introduce a controlled volume of the medium.

An alternative method is to insert the electrode and the medium together (e.g. simultaneously) so that the electrode surface is not exposed to deleterious materials, for example air or oxygen. This can be done by:

(a) insertion of a trocar cannula followed by the protective medium and then the electrode;

(b) using a pair of needles (especially a concentric pair of needles), of which one needle (preferably the central one of a concentric pair) is an electrode and the other is adapted to provide a supply of the protecting medium around the electrode as it is inserted. (The protecting medium (e.g. buffer solution) can then be trickled from a supply reservoir or can reach the needle tip by capillarity.

(c) using an electrode which is coated with a protecting medium which is in a form which is sufficiently stable and durable mechanically to remain in place to protect the electrode surface during the stage of its introduction into the in vivo site and thereafter either be dissipated or displaced by the bodily fluids to be monitored;

(d) using a cannula containing the protecting medium and introducing this until its exit tip is at the desired site for the electrode and then introducing the electrode through the cannula and the protecting medium therein so that it reaches the desired site for use.

In these forms (c) and (d), the protecting medium may be in the form of a viscous fluid or a gel, or the like, and especially a hydrophilic gel. Such a form of protecting medium should be of sufficient viscosity or strength to be able to remain in place during the critical stage of introduction in the subject.

One form of electrode for this purpose may have the protecting medium on the electrode surface as a membrane or impregnated in a membrane.

Another form of construction which offers considerable advantages is a needle with a recessed tip, within which the electrode is located within the tip but set back from the open tip of the needle, and the protecting medium is fed to the recess in the tip. This allows the protecting medium to be fed into the recess at the tip, thus interposing itself between the electrode and the tissue into which the needle is inserted.

A modification of this form of construction is that in which the recess at the tip of the needle contains a gel or hydrogel, which has the ability to remain in position there without flowing out, as a liquid would do. This facilitates the maintenance of the desired protecting environment and retention of the protecting medium with the minimum need to replenish this. The gel may be impregnated with the appropriate liquid medium before the needle/electrode is inserted into the tissue which it is desired to monitor. If desired, the efficiency can be improved or safeguarded by making provision for a supply of the protection medium (liquid) to be fed in, intermittently or continuously, as may be found necessary or desirable to maintain the electrode in good working condition and stable. The gel may be any of those materials indicated and discussed above in connection with the modes for increasing the viscosity of the protecting medium.

The supply of protecting medium (liquid) to the gel should be kept at a sufficient level to maintain the activity and the reliability of the electrode in use, while ensuring that the supply does not become excessive and risk causing any detrimental effects to the surrounding tissue, for example by "flooding" it with injected medium or disturbing the tissue to such an extent that the signal output from the electrode is debased because it is made more remote from the tissue which is being monitored.

Examples of solution volumes and compositions which may be used include (but only for exemplification and not limitation):

(a) Isotonic strength, mOsm of 275–295.
(b) Temperature of 21–37 degrees C.
(c) Hydrogel layer thickness, approximately 1–100 μm.
(d) Recessed tip dimensions: 0.02–2 mm diameter×0.2–5 mm depth.
(e) Volume of liquid introduced with the insertion of the needle/electrode: up to about 0.2 ml initially. Larger or smaller volumes may be used if desired, and the volume chosen will depend upon such factors as the overall distribution in the tissue. Thus 0.2 ml may suffice to hydrate the electrode tip (the gel zone) or 0.5 ml may in addition hydrate a large "field" or zone around the electrode/needle tip and provide better protection.
(f) proportions of components: approximating to the ranges of each natural component as found in blood plasma (see "Clinical Chemistry," by N. B. Tietz, for fuller details).

The electrodes may be made as very small items, especially in needle form to facilitate insertion into the site of use. In consequence, they may be made small enough to reach practically any site. Also, they can be made with such a simple construction that they may be treated as disposable after use.

According to our invention we also provide a novel and advantageous way for storing and selling the electrodes. This relies upon first making the electrode in a form which is clean and stable, for example by being packed in a protecting medium as described above, and then sealing it in a sterilised package and marking the package with details requisite for its use.

Such procedures and details may include calibration. This may be done very conveniently in a central facility, for example at the manufacturing site or the distribution/storage site. Then the data of the calibration may be put upon the package in any manner which is useful for convenient and or speedy use by the clinician. For example, the relevant data can be in coded form, especially a machine-readable form (for example a bar code or a magnetically recorded format) so that the user can, by means of a conventional "reading" device, "read" the encoded data into the user equipment so that the associated instrumentation equipment can assimilate the data and automatically make any adjustments which may be required to ensure that the read-out can be accurate without the need for further correction before it can be fit for being recorded.

The present invention has the advantage that the depression of the electrode output readings can be brought into close match with those obtained in in vitro use. This makes the use of the electrodes much more convenient and consistent, as well as allowing the use in vivo of electrodes which hitherto have really been of real practical value only in vitro.

The invention has the advantage of overcoming the problems arising from the fact that tissue is not very fluid and has a low water content (problems which make it difficult for diffusion of an analyte to the electrode), and the introduction of aqueous media into tissue in the manner described can "open up" tight tissue environment and improve diffusion and also stop turgid tissue from tightly compressing the electrode surface. Further, locally added components can reduce the biochemical effects leading to coagulation of any blood from broken capillaries, and operate by other mechanisms to maintain water or electrolyte around the electrode for a longer period and thereby extend the period of operability of the electrode. The invention also provides a conduit which allows for a more convenient and valuable calibration of the electrode in vivo or in situ.

We claim:

1. A method for monitoring various body parameters which comprises the steps of installing an electrode in place in vivo, providing, at a site of introduction of the said electrode, a liquid protecting medium having the properties of (a) suppressing adverse depressive effects on the electrode's output induced by the biological environment at the site of introduction of the electrode in the absence of the protecting medium and (b) not injuring the biological environment around the site of introduction of the electrode, and flowing the protecting medium into the biological environment, and wherein the liquid protecting medium is introduced into the site in which the electrode is to be used prior to the insertion of the electrode, and measuring signal outputs of the electrode to provide a measure of the body parameter being monitored.

2. A method as claimed in claim 1 which comprises modifying or replacing the protecting medium by contacting the protecting medium with an aqueous surrounding medium which allows the electrode to become exposed to the bodily biochemical changes of the surrounding environment which is to be monitored.

3. A method as claimed in claim 1 wherein the protecting medium is one or more of the following:

(a) an isotonic solution, substantially isotonic with the in vivo medium to be monitored;

(b) a buffer solution, compatible with the in vivo medium to be monitored, to avoid large pH changes which in turn may affect the electrode signal size; and/or (c) an anti-coagulant, which serves to reduce the changes of coagulation over a surface of the electrode or any part of its structure.

4. A method as claimed in claim 3 wherein the isotonic solution (a) is an aqueous saline solution containing one or more additives.

5. A method as claimed in claim 3 wherein the buffer solution (b) is based on phosphates and is aimed at producing or maintaining a pH of about 7.0 to 7.8.

6. A method as claimed in claim 3 wherein the protection medium is an isotonic buffer solution.

7. A method as claimed in claim 1 wherein the protecting medium contains one or more components which dissolve oxygen and serve as reservoirs for oxygen to prevent oxygen starvation and/or the oxygen and/or co-factors necessary for the functions of an oxidase-based enzyme electrode.

8. A method as claimed in claim 1 wherein the protecting medium contains an "active" component in a "slow-release" form.

9. A method as claimed in claim 1 wherein the protecting medium contains a material which raises the viscosity of the liquid.

10. A method as claimed in claim 1 or claim 2 wherein the electrode is a metal electrode, a membrane-covered electrode, an oxidase-based enzyme electrode, a de-hydrogenase-based enzyme electrode or an oxygen electrode.

11. In a method for monitoring various body parameters of a biological environment in which an electrode is installed at a site in the biological environment and then measurements of signal outputs of the electrode provide a measure of the parameters of the biological environment being monitored, the improvement which comprises supplying at the site of introduction of the electrode an effective amount of a liquid protecting medium sufficient to suppress the adverse depressive effects of the biological environment on the electrode's output at the time of and subsequent to introduction of the electrode into tissue at the site, and introducing the liquid protecting medium into the site prior to insertion of the electrode into tissue at the site.

12. A method according to claim 11 wherein the liquid protecting medium is modified or replaced with an aqueous surrounding medium to expose the electrode to biochemical changes of the body parameters being monitored.

13. A method for installing and using an electrode for monitoring parameters of a biological environment which comprises the steps of installing an electrode in place in vivo at a site in the biological environment, providing at the site of introduction of the said electrode, a liquid protecting medium having the properties of (a) suppressing adverse depressive effects on the electrode's output induced by the biological environment at the site of introduction of the electrode in the absence of the protecting medium and (b) not injuring the biological environment around the site of introduction of the electrode, and allowing the protecting medium freedom to flow into the biological environment, and introducing the liquid protecting medium through a cannula into the site at which the electrode is to be used, prior to insertion of the electrode, and measuring the electrode's output to provide a measure of the parameters of the biological environment being monitored.

14. In a method for using an electrode in place in vivo in a monitoring system for monitoring various body parameters, the improvement which comprises supplying at a site of introduction of the electrode an effective amount of a liquid protecting medium sufficient to suppress the adverse depressive effects of the biological environment on the electrode's output at the time of and subsequent to introduction of the electrode into tissue at the site, introducing the liquid protecting medium through a cannula into the site prior to insertion of the electrode into tissue at the site, and measuring the electrode's output to provide a measure of the parameters of the biological environment being monitored.

15. In a method for electrochemical monitoring parameters of a biological environment in which an electrode is installed in place by insertion into the biological environment and then measurements of signal outputs of the electrode are used to provide a measure of the parameters of the biological environment in which the electrode is installed, the improvement which comprises introducing, at the site of introduction of the electrode where measurements are to be made and prior to the insertion of the electrode into tissue at the site, an amount of a liquid protecting medium which serves to intervene between the electrode and the biological environment surrounding it, and (1) suppresses any adverse effects which the biological environment could have on the unprotected electrode's output at the time of and subsequent to the introduction of the electrode into tissue at the site, (2) prevents injury to the biological environment around the site of introduction of the electrode and (3) allows the introduced liquid protecting medium freedom to flow into the surrounding biological environment.

16. A method according to claim 15 wherein the liquid protecting medium is introduced through a cannula into the site at which the electrode is being used, prior to the insertion of the electrode.

17. A method according to claim 15 wherein the liquid protecting medium is modified or replaced with an aqueous surrounding medium which exposes the electrode to the surrounding biological environment sufficiently to permit monitoring its parameters.

* * * * *